United States Patent
Grey et al.

(10) Patent No.: US 7,030,255 B2
(45) Date of Patent: *Apr. 18, 2006

(54) OXIDATION PROCESS WITH IN-SITU H2O2 GENERATION AND POLYMER-ENCAPSULATED CATALYSTS THEREFOR

(75) Inventors: Roger A. Grey, West Chester, PA (US); Bi Le-Khac, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 74 days.

This patent is subject to a terminal disclaimer.

(21) Appl. No.: 10/796,680

(22) Filed: Mar. 9, 2004

(65) Prior Publication Data

US 2005/0202957 A1    Sep. 15, 2005

(51) Int. Cl.
 *C07D 301/06* (2006.01)
 *B01J 29/06* (2006.01)

(52) U.S. Cl. ............... 549/532; 549/523; 549/524; 502/64; 502/66; 502/74

(58) Field of Classification Search ............... None
See application file for complete search history.

(56) References Cited

U.S. PATENT DOCUMENTS

| | | | | |
|---|---|---|---|---|
| 4,043,941 | A * | 8/1977 | White et al. | 502/171 |
| 4,410,501 | A | 10/1983 | Taramasso et al. | 423/326 |
| 5,859,265 | A * | 1/1999 | Muller et al. | 549/531 |
| 5,973,171 | A | 10/1999 | Cochran et al. | 549/533 |
| 6,005,123 | A | 12/1999 | Dessau et al. | 549/531 |
| 6,063,942 | A | 5/2000 | Grey | 549/523 |
| 6,156,245 | A | 12/2000 | Takebayashi et al. | 264/4.7 |
| 6,252,095 | B1 * | 6/2001 | Hayashi et al. | 549/523 |
| 6,310,224 | B1 | 10/2001 | Grey | 549/523 |
| 6,403,815 | B1 * | 6/2002 | Grey | 549/532 |
| 6,498,259 | B1 | 12/2002 | Grey et al. | 549/533 |
| 6,534,661 | B1 * | 3/2003 | Zhou et al. | 549/531 |

FOREIGN PATENT DOCUMENTS

WO    WO 03/014014    2/2003

OTHER PUBLICATIONS

P. Kumar et al., *Synlett.* (1995) 289.
W. R. Sanderson, *Pure Appl. Chem.* 72 (2000) 1289.
Ingallina et al., *Sci. Tech. Catal.* (1994) 31.
T. Tatsumi et al., *J. Chem. Soc., Chem. Commun.* (1992) 1445.
S. Kobayashi et al., *Chem. Commun.* (2003) 449.
S. Kobayashi et al., *Andew. Chem., Int. Ed. 40* (2001) 3469.
S. Kobayashi et al., *J. Am. Chem. Soc. 120* (1998) 2985.
K. Edler et al., *J. Chem. Soc., Chem. Commun.* (1995) 155.
M. Donbrow, "Microcapsules and Nanoparticles in Medicine and Pharmacy" Ed., pp 1-4.
G. Beestman, "Microencapsulation of Solid Particles," in *Controlled-Release Delivery Systems for Pesticides* (1999), H. Scher, Ed., pp 31-54.
M. Iso et al., *Zairo Gijutsu 3* (1985) 29.
M. Yoshida, et al., *J. Appl. Polym. Sci. 89* (2003) 1966.
S. Ley et al., *Chem. Commun.* (2002) 1132 and 1134.
J. Yu et al., *Chem. Commun.* (2003) 678.
H. Kage et al., *Adv. Powder Technol. 13* (2002)265.
Y. Hu et al., *Chem. Commun.* (2002) 788.

(Continued)

*Primary Examiner*—Christina Johnson
(74) *Attorney, Agent, or Firm*—Jonathan L. Schuchardt

(57) ABSTRACT

Catalysts useful for oxidation reactions are disclosed. The catalysts comprise a titanium zeolite, a transition metal, and a polymer, wherein at least one of the titanium zeolite or transition metal is encapsulated within a thin layer of the polymer. The catalysts are easy to prepare and use, they are easy to recover and reuse, and they provide good conversions in a variety of important oxidation processes, including propylene epoxidation. The invention includes a process which comprises oxidizing an organic compound in the presence of hydrogen, oxygen, and the catalyst, wherein the transition metal catalyzes formation of hydrogen peroxide in situ.

24 Claims, No Drawings

OTHER PUBLICATIONS

W. Chen et al., *Tetrahedron 58* (2002) 3889.
D. Bergbreiter et al., *Org. Letters 2* (2000) 393.
O. Chiantore et al., *Polym. Degrad. Stab. 67* (2000) 461.
W. Chen et al., *Chem. Commun.* (2000) 839.
L. Balducci et al., *Angew. Chem. Int. Ed. 42* (2003) 4937.
C. Perego et al., *Appl. Catal. A 221* (2001) 63.
H. Ichihashi et al., *Appl. Catal. A 221* (2001) 359.
A. Bhaumilk et al., *Catal. Letters 40* (1996) 47.

* cited by examiner

OXIDATION PROCESS WITH IN-SITU H2O2 GENERATION AND POLYMER-ENCAPSULATED CATALYSTS THEREFOR

FIELD OF THE INVENTION

The invention relates to an oxidation process catalyzed by a titanium zeolite in which hydrogen peroxide is generated in situ.

BACKGROUND OF THE INVENTION

Titanium zeolites, i.e., synthetic molecular sieves that incorporate titanium atoms in a silicate framework, catalyze a wide variety of valuable oxidative organic reactions. The versatility of titanium zeolites, particularly TS-1, for arene hydroxylation, alkane oxidation, olefin epoxidation, thioether oxidation, Baeyer-Villiger oxidation reactions, and other important transformations is well known. For a review, see P. Kumar et al., *Synlett.* (1995) 289. Despite their obvious value for oxidation chemistry, titanium zeolites have apparently not been encapsulated within a polymer prior to their use to catalyze oxidation reactions.

For many titanium zeolite-catalyzed oxidations, hydrogen peroxide is the oxidant of choice. With a high active oxygen content and water as the only by-product, easy-to-use hydrogen peroxide has the potential to contribute to a "cleaner chemical industry" (see *Pure Appl. Chem.* 72 (2000) 1289). A key hurdle, however, is cost. Because hydrogen peroxide is relatively expensive, scientists continue to investigate ways to generate it "in situ" from molecular hydrogen and oxygen, usually in the presence of a platinum-group transition metal such as palladium. In situ-generated hydrogen peroxide has been used with titanium zeolites for propylene epoxidation and the oxidation of alkanes to alcohols and ketones (see *Sci. Tech. Catal.* (1994) 31) as well as benzene hydroxylation (*J. Chem. Soc., Chem. Commun.* (1992) 1446). It is presumably applicable to a variety of oxidation processes that utilize hydrogen peroxide. For additional examples of propylene epoxidations with titanium zeolites and in situ-generated hydrogen peroxide, see U.S. Pat. Nos. 5,973,171, 6,005,123, 6,063,942, 6,310,224, and 6,498,259.

Recently, Professor Sho Kobayashi reviewed a new kind of catalyst based on a technique called "microencapsulation" (see *Chem. Commun.* (2003) 449 and references cited therein; *Angew. Chem., Int. Ed.* 40 (2001) 3469; *J. Am. Chem. Soc.* 120 (1998) 2985). While polymer encapsulation has been used for years by the pharmaceutical industry to mask taste, impart storage stability, reduce stomach irritation, target delivery, or control release of drugs, benefits of the technique for catalysis are just now being realized. Kobayashi demonstrated that highly efficient catalysts can be made if the metals are enveloped within a thin polystyrene film. Microencapsulated transition metal catalysts and ways to make them are described in the *Chem. Commun.* article referenced above. These have been used for etherification, olefin dihydroxylation, allylic substitution, Suzuki coupling, and other organic transformations.

In sum, the value of microencapsulating transition metals for many organic reactions has been demonstrated, including at least one oxidative reaction (olefin dihydroxylation). Still unexplored, however, are oxidation reactions that use, as a catalyst, combinations of titanium zeolites and transition metals wherein at least one of these is encapsulated within a polymer.

SUMMARY OF THE INVENTION

The invention is a catalyst useful for oxidation reactions. The catalyst comprises a titanium zeolite, a transition metal, and a polymer, wherein at least one of the titanium zeolite or transition metal is encapsulated within a thin layer of the polymer. The catalysts are easy to prepare and use, they are easy to recover and reuse, and they provide good conversions in a variety of important oxidation processes. Thus, the invention includes a process which comprises oxidizing an organic compound in the presence of hydrogen, oxygen, and the catalyst, wherein the transition metal catalyzes formation of hydrogen peroxide in situ.

In one example, propylene reacts with hydrogen and oxygen in the presence of a polymer-encapsulated palladium catalyst and admixed titanium zeolite to produce propylene oxide. Surprisingly, polymer encapsulation of the palladium has little or no negative impact on the catalyst's ability to generate hydrogen peroxide in situ. Additionally, the use of a phosphine-functionalized polymer to encapsulate the titanium zeolite provides an unexpected and valuable reduction in the formation of propane (via hydrogenation of propylene) and thus enhances selectivity to propylene oxide.

DETAILED DESCRIPTION OF THE INVENTION

Catalysts of the invention include a titanium zeolite. Titanium zeolites are well-characterized, crystalline synthetic silicates or aluminosilicates that incorporate titanium atoms in the framework. The choice of titanium zeolite used depends upon many factors, particularly the type of organic reaction that it will catalyze and the identity of the reactants. In olefin epoxidations, for example, the choice of zeolite depends on the size and shape of the olefin to be epoxidized. It is preferred to use a relatively small pore titanium zeolite such as titanium silicalite if the olefin is a lower olefin such as ethylene, propylene, or 1-butene. When the olefin is propylene, TS-1 is particularly preferred. For a bulky olefin such as cyclohexene, a larger pore titanium zeolite such as a titanium zeolite having a structure isomorphous with zeolite beta is preferred.

Particularly preferred titanium zeolites include the class of molecular sieves commonly called titanium silicalites, particularly TS-1 (which has a topology similar to ZSM-5), TS-2 (which has a topology similar to ZSM-11), and TS-3. Also suitable are titanium zeolites that have framework structures isomorphous to zeolite beta, mordenite, ZSM-48, ZSM-12, and MCM41. Preferred titanium zeolites contain no elements other than titanium, silicon, and oxygen in the lattice framework, although minor amounts of boron, iron, aluminum, or the like may be present. Titanium silicalites, such as TS-1, are most preferred. TS-1 can be made by any known method. See, e.g., U.S. Pat. No. 4,410,501, the teachings of which are incorporated herein by reference, and *J. Chem. Soc., Chem. Commun.* (1995)155.

The catalyst includes a transition metal. Suitable transition metals are found in Groups 7–11. The first row of these, for example, includes transition metals from Mn to Cu. Preferred transition metals are Re, Au, and the metals of Groups 8–10. Particularly preferred are Re, Fe, Ru, Co, Rh, Ir, Ni, Pd, Pt, Ag, and Au. The transition metal can be present in any suitable form as long as it is capable of catalyzing the reaction between hydrogen and oxygen gases to make hydrogen peroxide. For example, it may be present as the free metal (e.g., Pt or Pd metal), as a mixture of metals (e.g., Pd—Au, Pd—Pt, or the like), or it may be part of a complex that incorporates the metal or metals and other ligands (e.g., PtCl$_2$, Pd(NH$_3$)$_4$Cl$_2$, tris(benzylideneacetone)dipalladium (0), or tetrakis(triphenyl-phosphine)palladium(0)). The transition metal or transition metal complex can be supported on silicas, aluminas, carbons, zeolites (e.g., titanium silicalites), clays, organic polymers such as crosslinked polystyrene, or any other conventional support prior to being encapsulated within a polymer. Other examples of transition metal sources suitable for use include Pd/C, Pt/C, Pd/silica, Pd/alumina, Pd/silicalite, PdNY-zeolite, Pd/kaolin, Pd/ZSM-5, Pd on TS-1, Pt on TS-1, Pd—Pt on TS-1, PdCl$_2$, PtCl$_2$, Pd(NH$_3$)$_2$Cl$_2$, PdBr$_2$, Pd(NO$_3$)$_2$, palladium(II) acetate, tetrakis(acetonitrile)palladium(II) bis(tetrafluoroborate), tetrakis(aceto-nitrile)palladium(II) bis(hexafluorophosphate), HAuCl$_4$, Au$_2$O$_3$, RhCl$_3$, IrCl$_3$, and the like.

At least one of the titanium zeolite or the transition metal is encapsulated within a polymer. By "encapsulated," we mean that the titanium zeolite, transition metal, or both, are contained within and are surrounded by a thin layer of polymer. Thus, encapsulation involves entrapping the zeolite, transition metal, or both, within a polymeric coating. To interact with the polymer-encapsulated catalyst species, reactants must penetrate the polymer coating.

Polymers suitable for use in making the catalysts are homopolymers or random and block copolymers produced by free-radical, ionic, or coordination polymerization of one or more polymerizable monomers. Generally, the polymers are natural or synthetic polymers made by addition or condensation polymerizations. Examples include polystyrenics, polyolefins, polyureas, polyacrylics, polyurethanes, polyesters, polyamides, fluorinated polymers, polysaccharides, polypeptides, polynucleotides, and the like, and mixtures thereof. Particularly preferred are polystyrenics, polyolefins, polyacrylics, and polyureas. The polymers can be generated by bulk, solution, suspension, or emulsion polymerization methods. The polymers can be hydrocarbons, or they can incorporate functional groups such as hydroxyl, amine, phosphine, phosphine oxide, arsine, sulfur, sulfur oxides, fluoroalkyl, alkoxy, silane, siloxy, carboxy, or the like.

There are many suitable ways to encapsulate transition metals and titanium zeolites within a polymer. Some of these techniques have been used to encapsulate pharmaceuticals to mask taste, impart storage stability, or target drug delivery; others have been used to encapsulate solid pesticide particles. Suitable techniques include, for example, spray-drying, spray-chilling, spray-coating, phase separation and coascervation, injection treatment coating, fluid bed coating, dry-on-dry coating, melt extrusion, vapor deposition, in-situ polymerization, including in-situ interfacial polymerization, and the like. These and other micro-encapsulation techniques are described in the introductory chapter of *Microcapsules and Nanoparticles in Medicine and Pharmacy*, M. Donbrow, Ed., pp. 1–14, and references cited therein, and in G. Beestman, "Microencapsulation of Solid Particles," *Controlled-Release Delivery Systems for Pesticides* (1999), H. Scher, Ed., pp. 31–54. See also U.S. Pat. No. 6,156,245.

Polymer encapsulation by phase separation/coascervation is one preferred technique. A suitable approach is illustrated by Kobayashi et al. (see *Chem. Commun.* (2003) 449 and references cited therein; *Angew. Chem. Int. Ed.* 40 (2001) 3469; *J. Am. Chem. Soc.* 120 (1998) 2985) with polystyrene as the polymer encapsulant. See also *Zairo Gijutsu* 3 (1985) 29, and *J. Appl. Polym. Sci.* 89 (2003) 1966.

In a particularly convenient coascervation approach, a modified version of the method of Kobayashi, polystyrene is dissolved in warm cyclohexane. The transition metal, titanium zeolite, or both, are dissolved or suspended in the mixture. Upon slow cooling to 0° C., phase separation and capsule formation occur. Hexane is added to harden the microcapsules, which are then isolated, washed, and dried.

In-situ polymerization is another preferred technique. The transition metal, titanium zeolite, or both, are dissolved or suspended in a reaction medium containing monomer(s), an initiator, and other components, and polymerization proceeds to give the polymer-encapsulated catalyst. The monomers can be hydrophilic (e.g., N,N-dimethylacrylamide), hydrophobic (e.g., styrene), or a combination of these. Suitable techniques include bulk, emulsion, suspension, and interfacial polymerizations.

One interfacial method is illustrated by Ley et al. (see *Chem. Commun.* (2002) 1132 and 1134; and *Chem. Commun.* (2003) 678) in the preparation of polyurea-encapsulated transition metals. In this example, an organic phase containing polymerizable monomers and the transition metal source is dispersed within an aqueous phase that contains emulsifiers and/or stabilizers. Polymerization occurs at the interface to form microcapsule walls. For another example of in-situ polymerization to generate microcapsules, see *Adv. Powder Technol.* 13 (2002) 265.

In another in-situ polymerization example, styrene or a mixture of styrene and other ethylenic monomer(s) is polymerized in an aqueous suspension according to well-known techniques in the presence of a dissolved or suspended transition metal source or titanium zeolite. The resulting polymer beads incorporate encapsulated transition metal, titanium zeolite, or both, and are suitable for use as an oxidation catalyst according to the process of the invention.

In another preferred approach, the polymer incorporates recurring units of a fluorinated monomer. Particularly suitable are fluorinated monomers made by reacting fluorinated alcohols with acrylic ester precursors. These and other suitable fluorinated monomers have been described previously (see *Chem. Commun.* (2002) 788; *Tetrahedron* 58 (2002) 3889, *Org. Letters* 2 (2000) 393, *Polym. Degrad. Stab.* 67 (2000) 461; and *Chem. Commun.* (2000) 839.) For example, polymerization of trifluoroethylmethacrylate (from methacryloyl chloride and trifluoroethanol) with styrene gives a fluorinated copolymer. Polymer encapsulation can be effected either in-situ or later by phase separation/coascervation.

Polymer-encapsulated catalysts of the invention are valuable for catalyzing a wide variety of oxidations in which hydrogen peroxide is generated in situ. Thus, the invention includes a process comprising oxidizing an organic compound in the presence of hydrogen, oxygen, and a polymer-encapsulated catalyst of the invention as described above. Suitable oxidation processes include arene hydroxylation to phenols or phenol hydroxylation to catechols (see, e.g., *Angew. Chem., Int. Ed.*, 42 (2003) 4937; *J. Chem. Soc., Chem. Commun.* (1992) 1446; and *Appl. Catal. A* 221 (2001) 63), alkane oxidation to oxygenated products such as alcohols and ketones (*Sci. Tech. Catal.* (1994) 31), olefin epoxidation (*Appl. Catal. A* 221 (2001) 63; *Sci. Tech. Catal.* (1994) 31), thioether oxidation (*Synlett.* (1995) 289), cyclohexanone ammoximation (*Appl. Catal. A* 221 (2001) 63, 359), Baeyer-Villiger oxidation reactions (*Catal. Letters* 40 (1996) 47), and other important transformations. For a general review, see *Synlett.* (1995) 289.

Optionally, the oxidation processes are performed in the presence of a solvent. The choice of solvent will depend on many factors, including the type of oxidation process, the solubilities of the reactants and products, the reaction conditions, the type of equipment, and other factors. Suitable solvents include, for example, water, alcohols, water/alcohol mixtures, oxygenated hydrocarbons (esters, ketones, ethers, or the like), aliphatic and aromatic hydrocarbons, liquid or supercritical carbon dioxide, amides, sulfoxides, and the like, and mixtures thereof. Preferred solvents are water, alcohols, carbon dioxide, and mixtures thereof.

In one preferred in-situ oxidation process, the organic compound is an olefin, and the oxidation product is an epoxide. In a particularly preferred process, the olefin is propylene and the epoxide is propylene oxide (see Examples 1–11 and Table 1 below). Suitable procedures and reaction conditions for making propylene oxide from propylene with titanium zeolites and hydrogen peroxide generated in situ have been described previously; see, e.g., U.S. Pat. Nos. 5,973,171, 6,005,123, 6,063,942, 6,310,224, 6,403,815, and 6,498,259, the teachings of which are incorporated herein by reference.

In another preferred oxidation process, the organic compound is a thioether, and the oxidation product is a sulfoxide, sulfone, or mixture thereof. Oxidation of thioethers is valuable for converting sulfide-containing impurities in fuel streams to more polar species that are more easily removed from the fuel. Example 15, below, illustrates the process.

Alkane oxidation to alcohols, ketones, or other oxygenated products is another preferred oxidation process of the invention. The process is valuable because the oxygenated products are usually expensive compared with unfunctionalized hydrocarbons. Example 16 shows how pentane can be oxidized in the presence of polymer-encapsulated palladium on TS-1 to give a mixture of C5 ketones and alcohols.

Other organic compounds can also be oxidized effectively using hydrogen peroxide and a polymer-encapsulated titanium zeolite of the invention. Thus, the invention includes oxidations of arenes to phenols, phenols to catechols, ketones to esters or lactones, ammoximation of aldehydes or ketones in the presence of ammonia or an amine to make oximes (e.g., the conversion of cyclohexanone to cyclohexanone oxime), and other oxidations known to be catalyzed by titanium silicalites (see *Synlett*. (1995) 289).

Polymer encapsulation of titanium zeolites and transition metals provides numerous advantages. First, polymer encapsulation makes it easy to recover the titanium zeolites and transition metals. When used in powder form, titanium zeolites or finely divided metals can blind filters or migrate undesirably in a reaction system. While this is sometimes remedied by converting the catalyst to a pellet or by spray drying it to increase particle size, such techniques are costly. Polymer encapsulation makes the particles easy to recover by ordinary filtration methods (see Example 17, Comparative Example 18, and Table 2 below). Moreover, recovered polymer-encapsulated titanium zeolites and transition metals can often be used without further processing.

Surprisingly, polymer encapsulation of the palladium or palladium on titanium silicalite has little or no negative impact on the catalyst's ability to generate hydrogen peroxide in situ. Propylene epoxidations proceed smoothly to provide good yields of propylene oxide (see Examples 1–7 and Comparative Examples 12–14, Table 1, below). When a phosphine-functionalized polymer is used to encapsulate the titanium zeolite, we observed an unexpected and valuable reduction in propane formation (see Examples 8–11 and Table 1). As shown in Example 11, phosphine-functionalization enables a higher proportion of $H_2$ to be used in the process, which provides a POE yield boost (versus Example 10) while maintaining a relatively low level of propane formation.

In sum, polymer-encapsulated transition metals and titanium zeolites are easy to prepare and use, they are easy to recover and reuse, and they provide good results in a variety of oxidation processes that are normally catalyzed by titanium zeolites and use in situ-generated hydrogen peroxide as an oxidant.

The following examples merely illustrate the invention. Those skilled in the art will recognize many variations that are within the spirit of the invention and scope of the claims.

Preparation of Polymer-Encapsulated Catalysts

EXAMPLE A

Preparation of Polystyrene-Encapsulated(Pd on TS-1)

Polystyrene beads (3.0 g) are dissolved in cyclohexane (60 g) at 50° C. using an ultrasonic bath. A sample of the warm solution (10.5 g) is combined with powdered Pd on titanium silicalite (2.0 g, 0.15 wt. % Pd on TS-1, prepared as described in Comparative Example H) and mixed at 50° C. for 1 h. Upon cooling the mixture to 0° C., coascervation occurs. Hexanes (20 g) are added to harden the capsules. The liquid portion is decanted, and the solids are resuspended in hexanes (80 g). The mixture is homogenized for about 1 minute and the liquid phase is decanted. The solids are dried under vacuum at 40° C. for about 1 h. The solids are then washed with methanol (80 g) and dried under vacuum overnight. Yield: 2.19 g. Pd: 0.08 wt. %; Ti: 1.7 wt. %. The product contains about 80 wt. % TS-1.

EXAMPLE B

Preparation of Polystyrene-Encapsulated Pd

Polystyrene beads (1.0 g) are dissolved in cyclohexane (20 mL) at 40° C. Tetrakis(triphenylphosphine)palladium(0) (Aldrich, 0.2 g) is added, and a clear solution results. Upon cooling the mixture to 0° C., coascervation occurs. Hexanes (50 mL) are added to harden the capsules. The liquid portion is decanted, and the solids are dried under vacuum at 40° C. The dry solids are ground to a powder prior to use. Pd: 0.96 wt. %; P: 1.19 wt. %; mole ratio of P/Pd: 4.26.

EXAMPLE C

Preparation of Polystyrene-Encapsulated Pd

Polystyrene beads (10.0 g) are charged to a one-liter glass reactor, followed by cyclohexane (190 g). The reactor is purged four times with helium. The mixture is heated to 40–50° C. to dissolve the polymer over 1–2 h. Tetrakis (triphenylphosphine)palladium(0) (1.0 g suspended in about 10 g of cyclohexane) is added by syringe, and mixing continues for 2 h as the mixture cools to room temperature and is chilled overnight.

Hexanes (400 mL) are added to the frozen mixture, which is homogenized for several minutes and is then decanted. The procedure is repeated with more hexanes (200 mL), and the recovered solids are dried under vacuum at 40° C. for 1–2 h. The dry solids are returned to the glass reactor. The reactor is purged with helium, and methanol (135 g) is added. After mixing 1–2 h at room temperature, the mixture sits under helium overnight.

The mixture is pressure filtered under nitrogen, and the solids are washed with methanol (3×75 mL). After vacuum drying at 40° C. for 1–2 h, the polymer-encapsulated palladium complex is recovered. Yield: 8.60 g; Pd: 0.92 wt. %; P: 0.77 wt. %; P/Pd: 2.9.

EXAMPLE D

Preparation of Polystyrene-Encapsulated(Pd on TS-1)

Polystyrene beads (7.0 g) are dissolved in cyclohexane (140 g) in a one-liter glass reactor at 45–50° C. over 1–2 h. Tetrakis(triphenyl-phosphine)palladium(0) (928 mg) suspended in cyclohexane (about 8 g) is added. TS-1 (14.0 g, calcined at 550° C.) is added, and mixing continues at 45–50° C. The mixture cools slowly to room temperature, and cold hexanes (about 400 mL) are added. After mixing thoroughly, the liquid portion is decanted. The solids are washed with additional hexanes, homogenized, and filtered. The recovered solids are dried under vacuum at 40° C. and crushed to a fine powder. Yield: 20.2 g. Pd: 0.31 wt. %; Ti: 0.88 wt. %; P: 0.24 wt. %; mole ratio P/Pd: 2.66.

EXAMPLE E

Preparation of Polystyrene-Encapsulated(Pd on TS-1)

Polystyrene beads (7.0 g) are dissolved in cyclohexane (140 g) in a one-liter glass reactor at 45–50° C. over 1–2 h. Tetrakis(triphenyl-phosphine)palladium(0) (463 mg) suspended in cyclohexane (about 8 g) is added to the reactor, which is kept under helium. TS-1 (14.0 g) suspended in cyclohexane (10 g) is added, and mixing continues at 45–50° C. for 2 h. The mixture cools slowly to room temperature and is chilled overnight.

Cold hexanes (200 g) are added and the liquid portion is decanted. More hexanes (200 g) are added, the mixture is homogenized, and liquids are decanted. The recovered solids are dried under vacuum at 40° C. and crushed to a fine powder.

The powder is resuspended in methanol (347 g) and stirred under nitrogen for 1–2 h. The mixture is filtered and the solids are again dried under vacuum. Yield: 20.4 g; Pd: 0.16 wt. %; P: 0.063 wt. %; Ti: 1.41 wt. %; mole ratio P/Pd: 1.35.

EXAMPLE F

Preparation of Ph$_2$P-Functionalized Polymer-Encapsulated(Pd on TS-1)

p-Styryldiphenylphosphine (20 g, 0.070 mol), styrene (25 g, 0.24 mol), and N,N-dimethylacrylamide (19.8 g, 0.20 mol) are dissolved in tetrahydrofuran (70 g) in a one-liter glass reactor. A solution of azobisisobutyronitrile (AIBN, 0.6 g) in tetrahydrofuran (2.5 g) is injected. After purging the stirred mixture well with nitrogen, it is heated to 80° C. for about 5.5 h. The reactor is cooled and the contents are removed. Removal of volatiles gives the desired phosphine-functionalized terpolymer. Tg=107° C.; peak mol. wt.=23,000; Mn=13,570; Mw=22,890; Mw/Mn=2.40.

A sample of the terpolymer (2.0 g) and tetrakis(triphenylphosphine)palladium(0) (69 mg) are dissolved in tetrahydrofuran (16 g). TS-1 (4.2 g) is mixed into the solution, and volatiles are removed by heating at 45° C. under vacuum. Yield: 6.12 g; Pd: 0.09 wt. %; P: 1.5 wt. %; N: 1.1 wt. %.

EXAMPLE G

Preparation of Ph$_2$P-Functionalized Polymer-Encapsulated(Pd on TS-1)

p-Styryldiphenylphosphine (16 g) is dissolved in toluene (100 mL) in a one-liter glass reactor. 4-t-Butylstyrene (60 g) is added, and the mixture is purged with nitrogen. A solution of azobisisobutyronitrile (AIBN, 0.5 g) in toluene (4 g) is injected, and the stirred mixture is heated to 85° C. for about 4.5 h. The reactor is cooled and the contents are removed. Yield of copolymer solution: 156 g. Wt. % solids: 43.0.

A sample of the copolymer/toluene solution (4.66 g, about 2.0 g of copolymer) is combined with tetrakis(triphenylphosphine)palladium(0) (132 mg), and the mixture is heated at 40° C. for 30 min. to give a clear, deep-yellow solution. TS-1 (6.0 g) is mixed into the solution, and volatiles are removed by heating at 45° C. under vacuum. The recovered catalyst is a dark-yellow powder. Yield: 7.89 g; Pd: 0.14 wt. %; Ti: 1.6 wt. %; Si: 31 wt. %.

COMPARATIVE EXAMPLE H

Preparation of 0.2 wt. % Pd on TS-1

A TS-1 (500 g, calcined in air at 550° C.; 2.1 wt. % Ti) is slurried in deionized water (700 mL). An aqueous solution of tetraammine-palladium(II) chloride (2.5 g in 35 g of deionized water) is added with mixing over 20 min. The round-bottom flask containing the slurry is turned at about 30 rpm in a water bath (30° C.) for 2 h. The slurry is pressure filtered; the cake is reslurried in deionized water (400 mL) and is refiltered. The washing step is repeated four times. The solids are air dried overnight, then dried under vacuum at 50° C. for 24 h to constant weight. Pd: 0.15 wt. %; Ti: 2.2 wt. %; Cl:<20 ppm.

COMPARATIVE EXAMPLE J

Preparation of 0.11 wt. % Pd on TS-1

A TS-1 powder (8.49 g, 0.2 micron, 1.6 wt. % Ti, calcined at 550° C. in air) is slurried in deionized water (12 g). An aqueous solution of tetraamminepalladium(II) nitrate (0.178 g aqueous solution containing 5.37 wt. % Pd, further diluted with 1.0 g of deionized water) is added with mixing over 1 min. The slurry is turned on a rotary evaporator to mix the slurry at 30° C. for 10 min. The pH is adjusted to 7.4 with 5% aqueous ammonium hydroxide. The slurry turns for an additional 30 min. and the pH is again adjusted to 7.4. The slurry is filtered. The filter cake is washed three times by reslurrying it in deionized water (15 g) and filtering. The solids are then air dried overnight and dried in a vacuum oven at 50° C. for 6 h. Pd: 0.11 wt. %; Ti: 1.5 wt. %.

The dried solids are oven calcined in air by heating from 23 to 110° C. at 10° C./min and holding at 110° C. for 2 h, then heating to 300° C. at 2° C./min and holding at 300° C. for 4 h. The calcined solids are then transferred to a quartz tube, heated to 50° C. and treated with 5 vol. % hydrogen in nitrogen (100 cm$^3$/min) for 4 h. After the hydrogen treatment, nitrogen is passed through the solids for 1 h before cooling to 23° C.

EXAMPLES 1–11 and COMPARATIVE
EXAMPLES 12–14

Propylene Epoxidation—General Procedure

A buffer solution (0.1 M, pH=6) is first prepared by dissolving ammonium dihydrogen phosphate ($NH_4H_2PO_4$, 11.5 g) in deionized water (900 g) and adding 30% aq. $NH_4OH$ solution to pH=6. The volume of the solution is then increased to exactly 1000 mL with deionized water.

A 300-mL stainless-steel reactor is charged with the catalyst shown in Table 1 (Catalysts A–H,. sometimes admixed with TS-1 as shown in the table), a portion of the buffer solution (13 g), and methanol (100 g). The reactor is charged with hydrogen (2%), oxygen (4%), propylene (5%), methane (0.5%), and nitrogen (88.5%) to give 300 psig in the reactor. Pressure is maintained in the reactor at a minimum of 300 psig, while feed gases are continuously passed through at 1.60 L/min (at 23° C., 1 atm). To maintain a constant solvent level in the reactor during the experiment, the oxygen, nitrogen, and propylene feeds are passed through a 2-L stainless-steel "saturator" vessel that contains methanol (1.5 L). The stirred reaction mixture is heated to 60° C., and the gaseous effluent is analyzed every hour by on-line gas chromatography. The liquid is analyzed by GC at the conclusion of the run (18 h). Results appear in Table 1.

EXAMPLE 15

In-Situ Oxidation of 2-Methylthiophene

A 100-mL Parr reactor is charged with polystyrene-encapsulated Pd on TS-1 (Catalyst A, 100 mg), methanol (18 g), deionized water (2.0 g), and 2-methylthiophene (43 mg). The reactor is closed, pressurized with nitrogen and vented to 1 atm. The reactor is then pressurized with hydrogen (to 100 psig), followed by a mixture of oxygen (4%) in nitrogen to a total of 1292 psig. The reactor is heated to 60° C. and allowed to react for 1 h. The reaction mixture is cooled to 23° C. and is analyzed by liquid chromatography. Analysis shows 25% conversion of 2-methylthiophene to oxidized products, including 2-methylthiophene oxide (a sulfoxide).

EXAMPLE 16

In-Situ Oxidation of Pentane

A 100-mL Parr reactor is charged with polystyrene-encapsulated Pd on TS-1 (Catalyst A, 200 mg), tert-butyl alcohol (20 g), and n-pentane (200 mg). The reactor is closed, pressurized with nitrogen and vented to 1 atm. The reactor is then pressurized with hydrogen (to 100 psig), followed by a mixture of oxygen (4%) in nitrogen to a total of 1292 psig. The reactor is heated to 60° C. and allowed to react for 2 h. The reaction mixture is cooled to 23° C. and is analyzed by gas chromatography. Analysisis shows 4% conversion of n-pentane to oxidized products, including 2-pentanone, 3-pentanone, 2-pentanol, and 3-pentanol.

TABLE 1

Propylene Epoxidations with In Situ-Generated $H_2O_2$

| Ex # | Cat | Catalyst Description and Amount[1] | Admixed[2] TS-1 (g) | Yield (g POE/g cat/h) | PO/ POE (%) | $C_3H_8$ (%) |
|---|---|---|---|---|---|---|
| 1 | A | PS-encap(Pd/TS-1) | 0 | 0.23 | 93 | 35 |
| 2 | B | PS-encap(Pd), 0.1 g | 0.6 | 0.33 | 86 | 14 |
| 3 | B | PS-encap(Pd), 0.2 g | 0.5 | 0.29 | 91 | 5 |
| 4 | C | PS-encap(Pd), 0.1 g | 0.6 | 0.23 | 92 | 7 |
| 5 | D | PS-encap(Pd/TS-1) | 0 | 0.17 | 93 | 6 |
| 6 | D | PS-encap(Pd/TS-1)[3] | 0 | 0.15 | 91 | 16 |
| 7 | E | PS-encap(Pd/TS-1) | 0 | 0.23 | 87 | 27 |
| 8 | F | $Ph_2P$-functionalized PS-encap(Pd/TS-1) | 0 | 0.09 | 96 | <1 |
| 9 | G | $Ph_2P$-functionalized PS-encap(Pd/TS-1) | 0 | 0.10 | 90 | <1 |
| 10 | G | $Ph_2P$-functionalized PS-encap(Pd/TS-1) | 0 | 0.14 | 90 | <1 |
| 11 | G | $Ph_2P$-functionalized PS-encap(Pd/TS-1)[4] | 0 | 0.19 | 89 | 2 |
| C12 | H | 0.2 wt. % Pd/TS-1 | 0 | 0.27 | 91 | 52 |
| C13 | H | 0.2 wt. % Pd/TS-1, 0.3 g | 0.4 | 0.27 | 91 | 25 |
| C14 | J | 0.11 wt. % Pd/TS-1 | 0 | 0.30 | 90 | 24 |

[1]Unless otherwise noted, 0.7 g of catalyst is used.
[2]TS-1 powder (0.2 micron, calcined in air at 550° C. to remove the template, 2.2 wt. % Ti) admixed with polymer-encapsulated catalyst before use.
[3]Catalyst reduced with hydrogen before use.
[4]$O_2/H_2$ ratio decreased to 1.3 for this run.

EXAMPLE 17 and COMPARATIVE EXAMPLE 18

Filterability Comparison

The filterability of polystyrene-encapsulated Pd/TS-1 is compared with Pd/TS-1 powder. Mixtures of Catalysts E or H in methanol/water (8:2 by volume, 50 mL) containing 1 wt. % of solids are prepared. The mixtures are filtered at 320 psig through a 2-μm filter, and the time needed to collect 20-mL and 40-mL samples is recorded. Results appear in Table 2.

The results demonstrate that Pd/TS-1 powder (Comparative Example 18) tends to plug the filter, resulting in a tedious filtration. Polymer encapsulation provides an easy, inexpensive way to make Pd on titanium zeolite oxidation catalysts that are easily recovered from the reaction mixture.

TABLE 2

Filterability of Polymer-Encapsulated Catalysts

| Ex. | Catalyst | Catalyst Source | Time to collect (min) 20-mL | 40-mL |
|---|---|---|---|---|
| 17 | PS-encap (Pd/TS-1) | E | <1 | <1 |
| C18 | Pd/TS-1 powder | H | 9 | 43 |

The preceding examples are meant only as illustrations. The following claims define the invention.

We claim:

1. A catalyst which comprises a titanium zeolite, a transition metal, and a polymer, wherein at least one of the titanium zeolite or transition metal is encapsulated within the polymer.

2. The catalyst of claim 1 wherein the titanium zeolite is TS-1.

3. The catalyst of claim 1 wherein the transition metal is selected from the group consisting of Pd, Pt, Ru, Rh, Re, Au, and mixtures thereof.

4. The catalyst of claim 1 wherein the transition metal is Pd.

5. The catalyst of claim 1 wherein the polymer is selected from the group consisting of polystyrenics, polyolefins, polyureas, polyacrylics, polyurethanes, polyesters, polyamides, fluorinated polymers, polysaccharides, polypeptides, polynucleotides, and mixtures thereof.

6. The catalyst of claim 5 wherein the polymer is polystyrene.

7. The catalyst of claim 1 wherein the polymer is a phosphorus-functionalized polystyrenic.

8. The catalyst of claim 1 comprising a polymer-encapsulated PdTS-1.

9. The catalyst of claim 1 comprising an admixture of TS-1 and polymer-encapsulated Pd.

10. The catalyst of claim 1 comprising an admixture of polymer-encapsulated TS-1 and supported Pd or a supported Pd complex.

11. A process which comprises oxidizing an organic compound in the presence of hydrogen, oxygen, and the catalyst of claim 1.

12. The process of claim 11 wherein the organic compound is propylene and the oxidation product is propylene oxide.

13. The process of claim 11 wherein the transition metal is Pd and the titanium zeolite is TS-1.

14. The process of claim 11 wherein the polymer is selected from the group consisting of polystyrenics, polyolefins, polyureas, polyacrylics, polyurethanes, polyesters, polyamides, fluorinated polymers, polysaccharides, polypeptides, polynucleotides, and mixtures thereof.

15. The process of claim 11 wherein the catalyst comprises a polymer-encapsulated Pd/TS-1.

16. The process of claim 11 wherein the catalyst comprises an admixture of TS-1 and polymer-encapsulated Pd.

17. The process of claim 11 wherein the catalyst comprises an admixture of polymer-encapsulated TS-1 and supported Pd or a supported Pd complex.

18. The process of claim 11 performed in the presence of a solvent selected from the group consisting of water, alcohols, carbon dioxide, and mixtures thereof.

19. The process of claim 11 wherein the organic compound is an arene and the oxidation product is a phenol.

20. The process of claim 11 wherein the organic compound is a phenol and the oxidation product is a catechol.

21. The process of claim 11 wherein the organic compound is a ketone and the oxidation product is an ester or a lactone.

22. The process of claim 11 wherein the organic compound is an aldehyde or a ketone, the process is performed in the presence of ammonia or an amine, and the oxidation product is an oxime.

23. The process of claim 11 wherein the organic compound is an alkane and the oxidation product is an alcohol, a ketone, or a mixture thereof.

24. The process of claim 11 wherein the organic compound is a thioether and the oxidation product is a sulfone, a sulfoxide, or a mixture thereof.

* * * * *